United States Patent [19]

Roussigne et al.

[11] Patent Number: 5,695,470
[45] Date of Patent: Dec. 9, 1997

[54] DEVICE FOR SUBCUTANEOUSLY LOCATING AN IMPLANTABLE MEDICAL APPARATUS

[75] Inventors: Maurice Roussigne; Guy Nadal, both of Poitiers; Gilles Bovyn, St Brieuc, all of France

[73] Assignee: B. Braun Celsa, Chasseneuil, France

[21] Appl. No.: 340,399

[22] Filed: Nov. 15, 1994

[30] Foreign Application Priority Data

Nov. 16, 1993 [FR] France ................... 93 13668

[51] Int. Cl.⁶ ................................................. A61M 5/00
[52] U.S. Cl. ................................................. 604/116
[58] Field of Search ........................ 604/116, 174; 128/899; 606/200

[56] References Cited

U.S. PATENT DOCUMENTS

| 2,625,934 | 1/1953 | Halliday | 606/200 |
| 2,670,730 | 3/1954 | Kellogg | 604/116 X |
| 3,017,887 | 1/1962 | Heyer | 604/116 X |
| 4,735,615 | 4/1988 | Uddo, Jr. et al. | |
| 5,009,644 | 4/1991 | McDonald | 604/116 X |
| 5,167,629 | 12/1992 | Vertenstein et al. | 604/116 |
| 5,171,228 | 12/1992 | McDonald | 604/116 X |
| 5,195,526 | 3/1993 | Michelson | 604/116 X |
| 5,300,086 | 4/1994 | Gory et al. | 606/200 |
| 5,360,407 | 11/1994 | Leonard | 604/116 X |
| 5,375,612 | 12/1994 | Cottenceau et al. | 128/899 |
| 5,454,364 | 10/1995 | Kruger | 604/116 X |
| 5,460,612 | 10/1995 | Madore | 604/116 |

FOREIGN PATENT DOCUMENTS

| 0 472 334 | 2/1992 | European Pat. Off. . |
| 0 521 222 | 1/1993 | European Pat. Off. . |
| 0 564 321 | 10/1993 | European Pat. Off. . |

Primary Examiner—Sam Rimell
Attorney, Agent, or Firm—Pollock, Vande Sande & Priddy

[57] ABSTRACT

A subcutaneous locating device for a blood filter is provided with a tubular component or catheter which can be perforated and is adapted so as to be implanted in a patient's body. The device comprises an external casing having a principal passage in order to receive therethrough a tubular component and a radial stud mounted so as to slide in the casing in order to perforate the tubular component and lock the casing along the latter under the control of an operator.

9 Claims, 1 Drawing Sheet

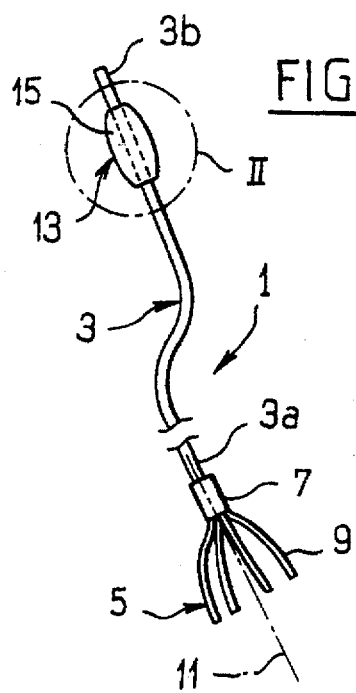
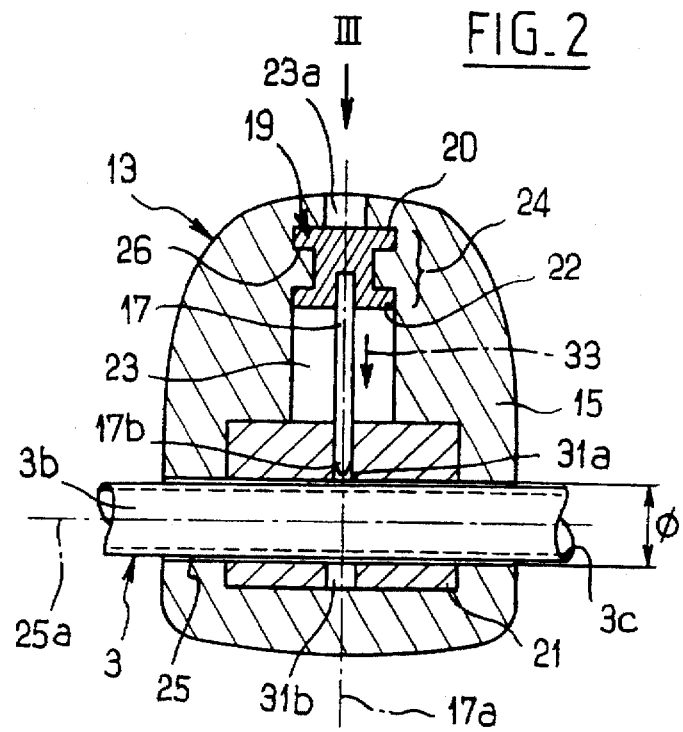
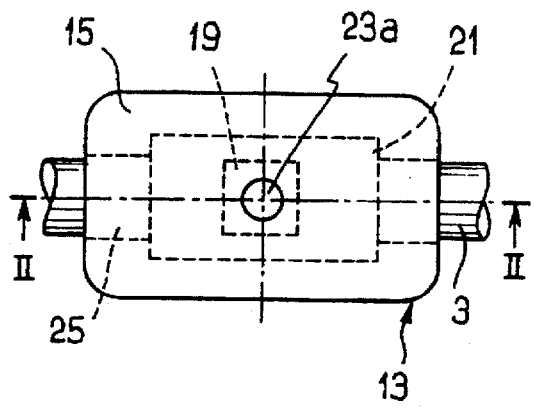
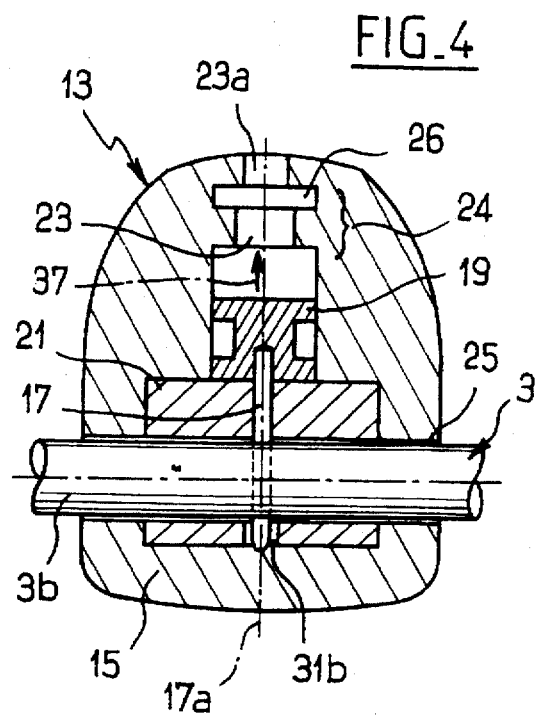

DEVICE FOR SUBCUTANEOUSLY LOCATING AN IMPLANTABLE MEDICAL APPARATUS

FIELD OF THE INVENTION

The invention relates to a device for subcutaneously locating a prosthesis or medical apparatus which comprises a tubular component and can be implanted in a patient's body, the device of the invention being in particular applicable to the locating by feel, through the patient's skin, of a catheter which can be perforated or the like and is conventionally associated with a temporary blood filter. The invention also relates to appliances thus equipped.

BACKGROUND OF THE INVENTION

In the area of vascular "prostheses" in particular which have to be able to be removed from the body at the end of a given period, when their presence in the vessel is no longer required, the catheters (or flexible rods) to which they are generally secured in order to enable them to be withdrawn, have particular features in given cases.

Thus, in particular in the area of temporary blood filters, it is today possible, for example, when a filter has to be implanted for several weeks, for the practitioner to cut the catheter to length, after implanting the filter, such that the proximal end of this catheter (the end opposite the end carrying the filter) does not emerge on the exterior of the patient's body. When this end has been cut, the practitioner secures about the catheter a locating member which he then disposes with the end of the catheter in a small accommodating device provided under the patient's skin, in the immediate vicinity of the access route used for implanting the filter. Thereafter, the practitioner only has to suture the flesh, allowing the filter and its catheter with its locating member to be concealed. When the filter is to be removed, it is sufficient for the practitioner to detect, for example, by feel, the location of the locating member to which he can gain access via a further small incision, enabling him to reach the catheter which can thus be removed or even moved to another location.

Subcutaneous locating devices of this type are already known in the art. Patent application FR 9000769 (or the corresponding U.S. patent application Ser. No. 07/731,536 of 17 Jul. 1991 and/or U.S. Pat. No. 5,300,086) provides one example thereof. A further example can be found in U.S. Pat. No. 4,834,713.

It will also be noted that, in addition to temporary blood filters, the prior art offers other types of medical prostheses which are associated with catheters or the like and which can thus be attached to a subcutaneous locating device (cf. publication EP 92402098.5).

As presented, the two above-mentioned locating devices, however, appear to have certain operating difficulties.

Thus, in order to be secured to the carrying catheter, the various versions of the "button" described in U.S. Pat. No. 4,834,713 require an internal metal collar to be deformed or even the cross-section of the internal passage of the button through which the catheter passes to be reduced locally.

Insofar as given traction stresses can be exerted on the carrying catheters once implanted, the retention of locating devices by simply restricting the cross-section can prove dangerous for the patient. Similarly, the local deformation of the device in order to enable it to be secured about the catheter can prove awkward and it may be difficult for the practitioner to assess the deformation force to be applied, which should be neither too slight (to ensure retention) nor too great (to avoid damaging the locating part or catheter).

Comparable problems can arise within the context of the solutions provided in publication FR 9000769. In particular, the final preferred solution in U.S. Pat. No. 5,300,086 (consisting of the use of a plug which can possibly be screwed into the internal passage of the catheter from its proximal end) can in practice prove awkward since the practitioner may possibly have difficulty in judging that the plug has engaged properly.

BRIEF DESCRIPTION OF THE INVENTION

In view of these existing solutions in particular, the object of the invention is more particularly:

to propose a subcutaneous locating device for a tubular prosthesis component which can be implanted and which is easily tolerated by the patient (non-aggressive);

to ensure that the locating device is positioned securely and reliably about the catheter or the like;

to facilitate the use of this device by the practitioner such that the latter can easily be sure that it has locked, without particular risk either for the patient or for the prosthesis;

possibly to permit disengagement of the locating device which should enable it either to be removed from the tubular component or its position along the latter to be changed while adhering to the above requirements; and to permit satisfactory production of the device and even of the entire prosthesis on an industrial scale.

In order to satisfy at least the essential points among those listed above, the invention thus proposes an improved subcutaneous locating device substantially characterized in that it comprises:

a casing of biocompatible material which has a principal passage passing through the casing along an axis, in order to receive the tubular component therethrough; and a blocking means or a perforation part passing through the casing in a direction transverse to the axis of the principal passage thereof in order to pass through, or engage in, the tubular component, under the control of an operator acting thereon, by thus blocking the locating device axially with respect to the tubular component.

In order to encourage satisfactory guiding of the above blocking means stud, with respect to the casing, an additional characteristic of the invention provides that the casing advantageously contains an internal collar which is not provided so as to be deformed and which has a wall surrounding an internal passage coaxial with the casing wall, this collar being disposed such that the locking stud passes through its wall and then passes through or perforates the tubular component.

Advantageously, both the stud and the collar are completely enclosed by the casing. In this manner, they could in particular be made of metal. In particular in this case, it may furthermore be preferable to produce the casing from a deformable material which is relatively flexible such that the operator can act from the exterior of the casing, for example manually, on the displacement of the stud, it being possible for the material used nevertheless to be selected such that the operator can distinguish the stud therethrough in particular in order to be able to assess more easily whether or not it is in the position in which it is engaged in the tubular component.

In order to maneuver this "stud", a further characteristic of the invention envisages that the stud can be associated with a maneuvering plunger which is bulkier than the latter, the plunger thus being easier to maneuver and locate through the casing, it being appreciated that an internal passage then has to be provided in the casing for its displacement in the transverse direction of the action of the stud.

According to an additional feature, the stud can furthermore have a cross-section which is far smaller than the internal diameter of the catheter, in particular such that the catheter support is not rendered more fragile.

Before a preferred embodiment of the device of the invention is described, it will further be noted that, for the patient's safety, the device preferably has no means of anchorage to the patient's body in particular avoiding the flesh being pulled or even torn.

For the sake of clarity, the following description is provided in relation to the appended drawings which are given solely by way of non-limiting example and in which:

BRIEF DESCRIPTION OF THE FIGURES

FIG. 1 shows a possible arrangement of the subcutaneous locating device of the invention from the proximal end of a vascular prosthesis in a generally schematic view;

FIG. 2 is a detailed view in median transverse section of the portion marked II in FIG. 1 (section along the line II—II of FIG. 3);

FIG. 3 is a plan view (completed by symmetry) in the direction of the arrow III of FIG. 2; and while FIG. 2 shows the locating device with its stud disengaged, FIG. 4 shows the same device with its stud perforating the catheter wall, according to the same sectional view.

DETAILED DESCRIPTION OF THE INVENTION

Since the locating device according to the invention can most particularly be associated with a temporary blood filtration instrument, only this embodiment will be described below, as it should be possible from the information contained in the present application and the technical knowledge of the person skilled in the art to enable the latter to adapt the device easily for use, for example, on an aterectomy device of the type mentioned in publication EP 92 402098.5.

FIG. 1 thus shows schematically a temporary filtration unit 1, which is perfectly conventional per se, comprising a catheter 3 (or any limp, flexible equivalent means such as a rod or filament) carrying a blood filter 5 which is secured thereto from its distal end 3a and which in this case consists of a connection head 7 which is crimped, for example, to the end 3a and in which a series of elongate fingers 9 extending substantially along the axis 11 of the device are combined. In order to perform their role of blood filter, these fingers can be expanded radially to the axis 11 such that they unfold in the form of a substantially conical corolla from their free end opposite the head 7.

For additional information relating to the filter or catheter, reference can be made to U.S. Pat. No. 5,300,086 or even to the French publication FR 92 09957 introduced into the present application by way of reference.

With respect to the catheter 3, it will, however, further be noted that it is made of a biocompatible material such as, for example, a silicone in order to adapt flexibly to the meanders of the implantation or access route which it has to follow in order to reach the installation location provided in the vessel.

In accordance with the invention, it should further be possible for this catheter to be passed through or perforated.

At its proximal end 3b it is further provided with a locating device 13 which externally can have a rounded shape, for example, it can be olive-shaped without sharp corners.

As illustrated in FIG. 2 in particular, the inventive device 13 comprises an external casing 15 of biocompatible material which is advantageously flexible or deformable. In this respect, the casing can in particular be made of silicone or the like which can have a hardness of between approximately 35 to 40 and 90 to 95 Shore A and preferably of the order of between 50 and 70 Shore A.

In the version illustrated, this casing or external sheath 15 contains a locking part or stud 17 of which the role is to lock the device 13 in position along the catheter 3. Also included is a plunger 19 for maneuvering the stud and a collar 21 through which the stud is to pass substantially radially in order to pass through or perforate the catheter. However, it should be evident that it would have been possible to reduce the cross-section of the passage 23 intended in this case for guiding the plunger 19 in translation such that the cross-section of this passage is adapted to the diameter of the stud 17 in order to dispense with the plunger while assisting the guiding of the stud along its displacement axis 17a. It would also have been possible to cause the stud 17 to emerge from the casing 15, in its disengaged position of FIG. 2, to enable the practitioner-operator to be able to push directly on the stud in order to engage it through the wall of the catheter until it is in its position shown in FIG. 4.

Irrespective of the variant selected, the displacement direction of the stud is transverse and preferably substantially perpendicular to the axis 25a of the principal internal passage 25 of the casing of which the diameter $\phi$ is preferably very slightly greater than the diameter of the catheter in order to enable the olive-shaped locating device 13 to be fitted easily about its proximal end 3b at the outset.

In the embodiment illustrated, the perforation part or stud 17 extends exclusively inside the transverse secondary passage 23—with the axis 17a—of the casing while being connected (for example engaged by force and/or bonded) from the end opposite its perforation tip 17b to the plunger 19 which is thus adapted such that it can also slide in the passage 23. In this respect, it will be noted that the plunger may have a cylindrical "T" shape according to a section in a plane containing the axis 17a (cutting plane of the FIG. 2) in order to render it easier to maneuver.

In order to avoid any awkward maneuvering of the plunger and/or of the stud in particular, the passage 23 which, at 23a, can communicate exclusively with the exterior, can locally have an area 24 for retaining the plunger when the stud is in the disengaged position (position shown in FIG. 2).

If the collar 21 is not made from a material which can be perforated, in the extension of the passage 23, it has a radial opening passing through the collar preferably from one side to the other, it being possible for the diameter of this aperture to be only slightly greater than that of the stud as concerns the part 31a in which the stud is permanently engaged in this case while, from the diametrically opposite side 31b, the diameter of the aperture can be larger.

The casing 15 can be positioned optimally as follows: when the casing has been fitted correctly about the catheter, the practitioner presses with his fingers on the part of the casing surrounding the plunger 19 which is then in its "rearward" position of FIG. 2 (stud in the immediate vicinity of the catheter wall 3c). The practitioner has to press sufficiently to release the plunger from its retaining area 24 of which the shoulder 26 in particular retains the rear flange 20 of the plunger. If the material of the casing has preferably been selected such that it is deformable, the pressure exerted thereon will tend to deform the area surrounding the plunger until it is released such that, under this thrust, it slides in the direction of the arrow 33 of FIG. 2, guided by flanges 20, 22. Entrained by the plunger, the stud then perforates the catheter wall 3c until it emerges on the diametrically opposite side in the aperture 31b. The plunger is then in the "forwards" position of FIG. 4, abutting the collar 21. It will be appreciated that it may be sufficient for the stud to penetrate the catheter without it necessarily emerging therefrom on the opposite side.

It will be noted that, if the material of the casing has been selected such that it is translucent or transparent, the practitioner can ensure that the stud engages correctly both by the tactile sensation felt and by checking visually. Whatever the case, the perforation of the catheter by the stud secures the position of the casing longitudinally.

In order to avoid weakening the catheter 3 (without thereby closing it), it may be advantageous for the diameter of the stud 17 to be less than the internal diameter of the catheter. A ratio of 3 to 4 can be appropriate.

If the material of the casing 15 is truly flexible, by further external pressure on this casing the practitioner may possibly entrain the plunger in the opposite direction (arrow 37 of FIG. 4) until it returns with the stud following it into the rearward position of FIG. 2, thus enabling the device 13 to be repositioned as necessary in some other location along the catheter. It should, however, be clear that there is no compulsion for the plunger to be able to return rearwards.

We claim:

1. A subcutaneous locating device for a medical apparatus all of which is completely enclosed within a patient's body, the apparatus including a tubular component, the locating device comprising:

a casing having a principal inner passage located along a preselected axis to be engaged around the tubular component and made from a deformable flexible material that yields under pressure from manual actuation to displace the piercing member that is entirely contained within the casing; and a piercing member slidingly mounted in the casing and displaceable along a direction transverse to the axis of the principal passage for piercing the tubular component in response to manual actuation that fastens the casing to the tubular component.

2. A removable subcutaneous locating device for a blood filtering apparatus all of which is completely enclosed within a patient's body, the apparatus including a pierceable catheter mounting a blood filter on a distal end thereof and the locating device on a proximal end thereof, the locating device comprising:

a casing having a principal inner passage located along a preselected axis to be engaged around the catheter;

means for fastening the casing along the length of the catheter, the fastening means further having a piercing stud slidingly mounted in the casing and located transverse to the axis of the principal passage for piercing the catheter in response to manual actuation; and the casing containing a maneuvering plunger connected to the stud, the plunger being displaceable in response to pressure exerted from the exterior of the casing and transmitted through the casing, the plunger being located in an internal space of the casing coaxial to the transverse direction of the displacement of the stud.

3. A device according to claim 1, in which the casing contains a collar which receives the tubular component, the collar having a passage transverse to the tubular component through which the piercing member is disposed.

4. A device according to claim 1, wherein the hardness of the casing is between approximately 50 and 70 Shore A.

5. A device according to claim 1, in which the casing further contains a maneuvering plunger connected to the piercing member, the plunger being displaceable in response to pressure exerted from the exterior of the casing and transmitted through the casing, the plunger located in an internal space of the casing coaxial to the transverse direction of the displacement of the piercing member.

6. A device according to claim 2, in which a cross-section of the stud is smaller than a internal cross-section of the catheter.

7. A device according to claim 2, in which the casing contains a collar which receives the catheter, the collar having a passage transverse to the tubular component through which the stud is slidingly mounted.

8. A device according to claim 2, in which the casing is made from a deformable flexible material that yields under pressure from manual actuation to displace the stud that is entirely contained within the casing.

9. A device according to claim 5, in which the maneuvering plunger is generally cylindrical with an axis parallel to that of the piercing member and having an "T"-shaped cross-section in a plane containing the axis of the piercing member.

* * * * *